(12) United States Patent
Singh et al.

(10) Patent No.: US 8,065,882 B2
(45) Date of Patent: *Nov. 29, 2011

(54) COMPOSITIONS CONTAINING FLUORINE SUBSTITUTED OLEFINS

(75) Inventors: Rajiv R. Singh, Getzville, NY (US); Hang T. Pham, Amherst, NY (US); Ian Shankland, Randolph, NJ (US); Raynond H. Thomas, Pendleton, NY (US); David P. Wilson, East Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/412,342

(22) Filed: Mar. 26, 2009

(65) Prior Publication Data

US 2009/0278076 A1 Nov. 12, 2009

Related U.S. Application Data

(60) Division of application No. 11/847,192, filed on Aug. 29, 2007, which is a division of application No. 10/837,525, filed on Apr. 29, 2004, now Pat. No. 7,279,451, which is a continuation-in-part of application No. 10/694,273, filed on Oct. 27, 2003, now Pat. No. 7,534,366, and a continuation-in-part of application No. 10/694,272, filed on Oct. 27, 2003, now Pat. No. 7,230,146.

(60) Provisional application No. 60/421,263, filed on Oct. 25, 2002, provisional application No. 60/421,435, filed on Oct. 25, 2002.

(51) Int. Cl.
*C09K 5/04* (2006.01)

(52) U.S. Cl. .............. 62/6; 252/68; 252/71; 252/78.1; 252/67; 62/401; 62/498

(58) Field of Classification Search .............. 252/67, 252/68, 71, 78.1; 62/6, 401, 498
See application file for complete search history.

(56) References Cited

U.S. PATENT DOCUMENTS

| | | | |
|---|---|---|---|
| 2,846,458 A | 8/1958 | Haluska | |
| 2,834,748 A | 10/1958 | Bailey et al. | |
| 2,889,379 A | 6/1959 | Ruh et al. | |
| 2,917,480 A | 12/1959 | Bailey et al. | |
| 2,931,840 A | 4/1960 | Maley | |
| 2,970,988 A | 2/1961 | Lo | |
| 2,996,555 A | 8/1961 | Rausch | |
| 3,085,065 A | 4/1963 | Kvalnes | |
| 3,085,918 A | 4/1963 | Sherliker et al. | |
| 3,472,826 A | 10/1969 | Potts et al. | |
| 3,607,755 A | 9/1971 | Murphy et al. | |
| 3,659,023 A | 4/1972 | Regan | |
| 3,723,318 A | 3/1973 | Butler et al. | |
| 3,884,828 A | 5/1975 | Butler | |
| 4,465,786 A | 8/1984 | Zimmer et al. | |
| 4,650,914 A | 3/1987 | Woodard | |
| 4,755,316 A | 7/1988 | Magid et al. | |
| 4,788,352 A | 11/1988 | Smutny | |
| 4,798,818 A | 1/1989 | Baizer et al. | |
| 4,900,874 A | 2/1990 | Ihara et al. | |
| 4,944,890 A | 7/1990 | Deeb et al. | |
| 4,945,119 A | 7/1990 | Smits et al. | |
| 4,971,712 A | 11/1990 | Gorski et al. | |
| 4,975,212 A | 12/1990 | Thomas et al. | |
| 5,008,028 A | 4/1991 | Jolley et al. | |
| 5,155,082 A | 10/1992 | Tung et al. | |
| 5,182,040 A | 1/1993 | Bartlett et al. | |
| 5,250,208 A | 10/1993 | Merchant et al. | |
| 5,254,280 A | 10/1993 | Thomas et al. | |
| 5,370,812 A * | 12/1994 | Brown | 252/68 |
| 5,532,419 A | 7/1996 | Van Der Puy et al. | |
| 5,545,777 A | 8/1996 | Morikawa et al. | |
| 5,574,192 A | 11/1996 | Van DerPuy et al. | |
| 5,578,137 A | 11/1996 | Shealy et al. | |
| 5,611,210 A | 3/1997 | Nimitz et al. | |
| 5,616,275 A | 4/1997 | Chisolm et al. | |
| 5,648,017 A | 7/1997 | Bartlett et al. | |
| 5,674,451 A | 10/1997 | Nimitz et al. | |
| 5,679,875 A | 10/1997 | Aoyama et al. | |
| 5,710,352 A | 1/1998 | Tung | |
| 5,714,083 A | 2/1998 | Turner et al. | |
| 5,728,904 A | 3/1998 | Van Der Puy et al. | |
| 5,736,062 A | 4/1998 | Basile | |
| 5,736,063 A | 4/1998 | Richard et al. | |
| 5,744,052 A | 4/1998 | Bivens | |
| 5,763,063 A | 6/1998 | Pass et al. | |
| 5,788,886 A | 8/1998 | Minor et al. | |

(Continued)

FOREIGN PATENT DOCUMENTS

EP 0398147 11/1990

(Continued)

OTHER PUBLICATIONS

Translation of JP4-110385, provided by applicant in U.S. Appl. No. 10/694,273 on Nov. 10, 2008.*
U.S. Appl. No. 10/694,273, filed Oct. 27, 2003, Singh et al.
U.S. Appl. No. 10/695,212, filed Oct. 27, 2003, Thomas et al.
U.S. Appl. No. 10/826,811, filed Apr. 16, 2004, Singh et al.
U.S. Appl. No. 10/826,592, filed Apr. 16, 2004, Singh et al.
U.S. Appl. No. 10/826,072, filed Apr. 16, 2004, Singh et al.
U.S. Appl. No. 10/837,525, filed Apr. 29, 2004, Singh et al.
Billy C. Langley, "Automotive Air conditioning," *Refrigeration and Air Conditioning*, 3d Ed. Prentice-Hall, (1986) pp. 525-526 US.
Althouse, et al., "Heat Pump Systems, Principles, Applications," *Modem Refrigeration and Air Conditioning*, Chapter 26, pp. 999, 1002-1003. The Goodheart-Wilcox Co., Inc. (1998) US.

(Continued)

*Primary Examiner* — Amina Khan
(74) *Attorney, Agent, or Firm* — Colleen D. Szuch

(57) ABSTRACT

Disclosed are the use of fluorine substituted olefins, including tetra- and penta-fluoropropenes, in a variety of applications, including connection with blowing agents, foams, foamable compositions, foaming methods, heat transfer compositions and methods, propellants, and solvating methods.

52 Claims, No Drawings

U.S. PATENT DOCUMENTS

| | | | |
|---|---|---|---|
| 5,792,383 | A | 8/1998 | Reyes-Gavilan et al. |
| 5,800,730 | A | 9/1998 | Bivens et al. |
| 5,811,603 | A | 9/1998 | Elsheikh |
| 5,866,030 | A | 2/1999 | Reyes-Gavilan et al. |
| 5,969,198 | A | 10/1999 | Thenappan et al. |
| 5,986,151 | A | 11/1999 | Van Der Puy |
| 6,023,004 | A | 2/2000 | Thenappan et al. |
| 6,025,532 | A | 2/2000 | Sage |
| 6,031,141 | A | 2/2000 | Mallikarjuna et al. |
| 6,041,621 | A | 3/2000 | Olszewski et al. |
| 6,045,444 | A | 4/2000 | Zima et al. |
| 6,059,027 | A | 5/2000 | Lake et al. |
| 6,076,372 | A * | 6/2000 | Acharya et al. ............. 62/606 |
| 6,089,032 | A | 7/2000 | Trachtenberg |
| 6,111,150 | A | 8/2000 | Sakyu et al. |
| 6,124,510 | A | 9/2000 | Elsheikh et al. |
| 6,173,902 | B1 | 1/2001 | Bauer et al. |
| 6,176,102 | B1 | 1/2001 | Novak et al. |
| 6,235,951 | B1 | 5/2001 | Sakyu et al. |
| 6,258,292 | B1 | 7/2001 | Turner et al. |
| 6,274,779 | B1 | 8/2001 | Merkel et al. |
| 6,300,378 | B1 | 10/2001 | Tapscott |
| 6,304,803 | B1 | 10/2001 | Dao |
| 6,316,681 | B1 | 11/2001 | Yoshikawa et al. |
| 6,327,866 | B1 | 12/2001 | Novak et al. |
| 6,369,284 | B1 | 4/2002 | Nappa et al. |
| 6,374,629 | B1 | 4/2002 | Oberle |
| 6,382,305 | B1 | 5/2002 | Sano |
| 6,516,837 | B2 | 2/2003 | Thomas et al. |
| 6,530,421 | B1 | 3/2003 | Filius et al. |
| 6,548,719 | B1 | 4/2003 | Nair et al |
| 6,589,355 | B1 | 7/2003 | Thomas et al. |
| 6,640,841 | B2 | 11/2003 | Thomas |
| 6,695,973 | B1 | 2/2004 | Musso |
| 6,783,691 | B1 | 8/2004 | Bivens |
| 6,809,226 | B1 | 10/2004 | Pennetreau et al. |
| 6,843,930 | B2 | 1/2005 | Cho |
| 6,858,571 | B2 | 2/2005 | Pham et al. |
| 6,958,424 | B1 | 10/2005 | Nair et al. |
| 6,972,271 | B2 | 12/2005 | Thomas et al. |
| 6,991,532 | B2 | 1/2006 | Goldsmith |
| 6,991,744 | B2 | 1/2006 | Mahler |
| 7,105,152 | B1 | 9/2006 | Schultz |
| 7,230,146 | B2 | 6/2007 | Merkel et al. |
| 7,279,451 | B2 | 10/2007 | Singh et al. |
| 7,345,209 | B2 | 3/2008 | Mukhopadhyay et al. |
| 2003/0127115 | A1 | 7/2003 | Thomas et al. |
| 2004/0119047 | A1 | 6/2004 | Singh et al. |
| 2004/0127383 | A1 | 7/2004 | Pham et al. |
| 2004/0256594 | A1 | 12/2004 | Singh et al. |
| 2005/0020862 | A1 | 1/2005 | Tung et al. |
| 2005/0054741 | A1 | 3/2005 | Zipfel et al. |
| 2005/0090698 | A1 | 4/2005 | Merkel et al. |
| 2005/0107246 | A1 | 5/2005 | Thomas et al. |
| 2005/0171391 | A1 | 8/2005 | Janssens et al. |
| 2006/0243944 | A1 | 11/2006 | Minor et al. |
| 2007/0069175 | A1 * | 3/2007 | Thomas et al. ............. 252/68 |
| 2007/0098646 | A1 | 5/2007 | Nappa et al. |
| 2007/0100010 | A1 | 5/2007 | Creazzo et al. |
| 2007/0108403 | A1 | 5/2007 | Sievert et al. |
| 2007/0284555 | A1 | 12/2007 | Leck et al. |
| 2008/0099190 | A1* | 5/2008 | Singh et al. ............. 165/104.21 |
| 2009/0272134 | A1* | 11/2009 | Hulse et al. ............. 62/112 |

FOREIGN PATENT DOCUMENTS

| | | |
|---|---|---|
| EP | 0522639 | 1/1993 |
| EP | 0644173 | 5/1993 |
| EP | 0 681 933 A1 | 11/1995 |
| EP | 0974571 | 1/2000 |
| EP | 1055439 | 11/2000 |
| EP | 1191080 | 7/2002 |
| EP | 0971571 | 4/2003 |
| GB | 950 876 | 2/1964 |
| JP | 8-157847 A | 0/1996 |
| JP | 63-211245 | 9/1988 |
| JP | 63-303950 | 12/1988 |
| JP | 4-110385 * | 4/1992 |
| JP | 04-110388 A | 4/1992 |
| JP | 10007604 | 10/1998 |
| JP | 11140002 | 5/1999 |
| JP | 2000169404 | 6/2000 |
| RU | 2073058 C1 | 12/1994 |
| WO | 95/04021 | 2/1995 |
| WO | 96/01797 | 1/1996 |
| WO | 98/33755 | 8/1998 |
| WO | WO 03064508 | 8/2003 |
| WO | 2004/37752 A2 | 5/2004 |
| WO | 2004/037913 | 5/2004 |
| WO | WO2004/037752 | 5/2004 |
| WO | 2005/012212 | 2/2005 |
| WO | 2005/42451 | 5/2005 |
| WO | 2005/042663 | 5/2005 |
| WO | 2005/103187 | 11/2005 |
| WO | 2005/103188 | 11/2005 |
| WO | 2005/103190 | 11/2005 |
| WO | 2005/103191 | 11/2005 |
| WO | 2005/103192 | 11/2005 |
| WO | 2005/0105947 | 11/2005 |
| WO | 2007/002625 | 1/2007 |

OTHER PUBLICATIONS

Meyer Kutz (Editor), "Refrigerants," *Mechanical Engineers' Handbook*, 2d Ed. p. 1887, John Wiley & Sons, Inc. (publ.) (1998) US.

Althouse et al., "Automobile Air Conditioning," *Modern Refrigeration and Air Conditioning*, Chapter 27, pp. 949-976. The Goodheart-Wilcox Co., Inc. (1988) US.

H. Michael Hughes, "Refrigerants," *Refrigeration Systems for HVAC*, Section 6, pp. 6.1.2-6.1.15, McGraw-Hill Co. (1997) US.

Society of Heating, Air-Conditioning and Sanitary Engineers, "Chapter 1. Refrigeration System and Heat Pump Overview," *Air Conditioning and Sanitary Engineering Handbook*, $12^{th}$ Ed. (Mar. 25, 1995) JP.

Sybil Parker (Ed.), *McGraw-Hill Encyclopedia of Engineering*, 2d Ed. (1993), p. 525 (Heat Pump). US.

M Spatz et al., "HFO-1234yf Low GWP Refrigerant," Presentation given at *SAE 2008 Alternate Refrigerant Systems Symposium*, Scottsdale (AZ), Jun. 10-12, 2008. US.

M Spatz et al., " HFO-1234yf Low GWP Refrigerant," Presentation given at International Refrigeration and Air Conditioning Conference at Purdue, Jul. 14-17, 2008 US.

LJM Kuipers, "Impact of the decreasein CFC Emissions on refrigeration: target of the IIR initiative," *Int. J. Refrigeration*, pp. 35-51, vol. 11, No. 6. (1988) US.

Directive 2006/40/EC of the European Parliament and of the Council of May 17, 2006 relating to emissions from air-conditioning systems in motor vehicles and amending Council Directive 70/156/EC. EU.

European Parliament Session Document. "Report On The Proposal For A European Parliament And Council Regulation On Certain Fluorinated Greenhouse Gases." (COM(2003)492-C5-0397/03-2003/0189(COD)), Mar. 18, 2004.

J Jones, CJ Morrissey, Nearly Azeotropic mixtures to replace refrigerant 12, *NASA Tech Brief*, vol 16, No. 8, Item #122 from JPL New Technology Report NPO 18030//528, pp. 1-39, Aug. 1992 US.

"Compatibility With Refrigeration Oil," Extract from the *Daikin Handbook*, Jun. 2001, pp. 25-28.

Sjoholm et al, "Twin-Screw Compressor Performance And Suitable Lubricants With HFC-134a," International Compressor Engineering Conference at Purdue (Jul. 17-20, 1990), Proceedings vol. II, pp. 733-740. US.

Honeywell's submission to EPO dated May 2, 2009 together with documents cited and referred to therein. EP(documents submitted herein are below (16a-16k).

Althouse et al., "Basic Air Conditioning Systems," *Modern Refrigeration and Air Conditioning*, Chapter 19, pp. 679-705. The Goodheart-Wilcox Co., Inc. (pub.) (1988) US.

Billy C. Langley, "Automotive Air Conditioning," *Refrigeration and Air Conditioning*, 3d Ed. Prentice-Hall, (1986) Chapter 21, pp. 525-553 US.

European Parliament, "Report on the proposal for a European Parliament and Council regulation on certain fluorinated greenhouse gases," (COM(2003)492-C5-0397/03-2003/0189(COD)) Mar. 18, 2004 (EP).

Pollution Prevention Fact Sheet No. 10, Pollution Prevention Program. Federal Programs Division, Managing Controlled Refrigerants, Jan. 1997, pp. 1-8 CA.
Graham, "Global Market for Heating, Ventilation and Air-Conditioning Systems," ABOUT Automotive —Research Report, 2006 Edition. GB.
Ignatio De Alvaro et al., "Market Report, Minisplits," BSRIA Report No. 18588/5, May 2004.
Emil Milker et al., "Worldwide Air Conditioning," BSRIA Report No. 19947B, BSRIA Limited, Mar. 2008, GB.
National Technical Information Service, U.S. Dept. of Commerce, Support: Letter from DuPont Haskell Lab to USEPA Regarding Results of Bacterial Reverse Mutation Assay Conducted With 1-Propene, 1,3,3,3-Pentafluoro-. Apr. 17, 2000.
Morrissey, C.J., "Nearly Azeotropic Mixtures to Replace Refrigerant 12," From National Aeronautics and Space Administration Contract No. NAS 7-918, Aug. 1992, NASA Tech Brief, vol. 16, No. 8, Item #122. US.
1234yf OEM Group, "Update: 1234yf as a replacement for R134a," publighed following MAC (Mobile Air-Conditioning) Summit in 2008, see pp. 14, 15 and 18.
PRNewswire, Honeywell's Low-Global-Warming-Potential Refrigerant Endorsed by SAE International Cooperative Research Project, Internet article, www.prnewswire.co.uk/cgi/news/release?id=244472 (Dec. 8, 2008) GB.
Takahashi, "Alternative Technologies for Refrigeration And Air-Conditioning Applications," *Environmental Chemistry of Chlorofluorocarbon and Control Engineering*, (Quarterly Issue of General Review of Chemistry, 1991, No. 11) JP.
Kenji Tojo, "Insulations Systems and Materials for Hermetic Motor," *Latest new refrigerant and insulation system technology*, Chapter 7, First Edition, (1996) JP.
Honeywell International Inc. Response to Notice of Opposition of Arkema France and exhibits cited therein.
Althouse et al., "Basic Air Conditioning Systems, " *Modern Refrigeration and Air Conditioning*, Chapter 19, pp. 679-705. The Goodheart-Wilcox Co., Inc. (pub.) (1988) US (previously cited).
Graham, "Global Market for Heating, Ventilation and Air-Conditioning Systems," ABOUT Automotive—Research Report, 2006 Edition. GB (previously cited).
Ignatio De Alvaro et al., "Market Report, Minisplits," BSRIA Report No. 18588/5, May 2004. (previously cited).
Milker, et al., "Report, Worldwide Air Conditioning," BSRIA, Report No. 19947B, Mar. 2008. GB.
Pollution Prevention Fact Sheet No. 10, Pollution Prevention Program. Federal Programs Division, Managing Controlled Refrigerants, Jan. 1997, pp. 1-8 CA (previously cited).
About MACS Worldwide, "Welcome to the Mobile Aire Conditioning Society (MACS) Worlwide," webpage printout http://www.macsw.org//AM/Template.cfm?Section=Home.
Billy C. Langley, "Automotive Air Conditioning," *Refrigerationand Air Conditioning*, 3d Ed. Prentice-Hall, (1986) Chapter 21, pp. 525-553 US (previously cited).
H. Kruse, "CFC Research Programmes In Western Europe," Int. J. Refrig. 1990, vol. 13 (Presented at the 1989 ASHRAE CFC Tecnology Conference, Gaithersburg, MD (Sep. 27-28, 1989). US.
Bivens et al., "Fluoroethers and Other Next-Generation Fluids," ASHRAE/NIST Refreigerants Conference—Oct. 1997.
Smith, New Chemical Alternatives for CFCs And HCFCs, U.S. Environmental Protection Agency, EPA-600/F-92-012 (Mar. 24, 1002) US.
J. Calm and D. Didion et al., "Trade-Offs in Refrigerant Selections: Past, Present, and Future," ASHRAE/NIST Refrigerant Conference—Oct. 1977.
Denis Clodic, "Automobile Air Conditioning: Environmental Issues and Future Technical Alternatives," The globalization of automobile air conditioning. General review of refrigeration and air conditioning, May 2008 (translation).
R. Gicquel, "Thermodynamic Diagrams—Mixtures Used in Refrigeration" FR.
Weiss et al., "Current and Projected use of Refrigerants in Europe," ASHRAE/NIST Refreigerants Conference—Oct. 1997.

2006 Standard for Sepcifications for Fluorocarbon Refrigerants, Standard 700—ARI (Air-Conditioning & Refrigerant Institute), copyright 2006.
J Jones, CJ Morrissey, Nearly Azeotropic mixtures to replace refrigerant 12, *NASA Tech Brief*, vol. 16, No. 8, Item #122 from JPL New Technology Report NPO 18033//528, pp. 1-39, Aug. 1992 US (previously cited).
Kopko, "Beyond CFCs: Extending the Search for New Refrigerants," Supplied by The British Library.
1234yf OEM Group, "Update: 1234yf as a replacement for R134a," published following MAC (Mobile Air-Conditioning) Summit in 2008, see pp. 14, 15 and 18. (previously cited).
PRNewswire, Honeywell's Low-Global-Warming-Potential Refrigerant Endorsed by SAE International Cooperative Research Project, internet article, www.prnewswire.co.uk/cgi/news/release?id=244472 (Dec. 8, 2008) GB (previously cited).
Clodic, Automobile Air Conditioning: Environmental Issues and Future Technical Alternatives, the New Refrigerant Fluids. (translation) (May 2008) FR.
"Arkema Beefs Up Chemicals; Eyes Acquisition of Acrylics Assets," Business & Finance News, Chemical Week, Nov. 17, 2008, p. 19.
Executed Assignment of Inventorship for U.S. Application, Honeywell Reference US.
Exeduted Declaration of Inventorship for U.S. Appl. No. 10/837,525, Honeywell Reference. US.
National Technical Information Service, U.S. Dept. of Commerce, Support: Letter from DuPont Haskell Lab to USEPA Regarding Results of Bacterial Reverse Mutation Assay Conducted With 1-Propene, 1,1,3,3,3-Pentfluoro—. Apr. 17, 2000 (previously cited).
Althouse et al., "Automobile Air Conditioning," *Modern Refrigerationand Air Conditioning*, Chapter 27, pp. 949-976. The Goodheart-Wilcox Co., Inc. (1988) US (previously cited).
Honeywell webpage printout, re: Honeywell Genetron Refrigerants, "Commercial AC Products," (Jul. 14, 2010) US.
Honeywell webpage printout, re: Honeywell Genetron Refrigerants, "Mobile A.C," (Jul. 14, 2010) US.
Honeywell webpage printout, re: Honeywell Genetron Refrigerants, "Genetron 134a," (Jul. 14, 2010) US.
OJ Nielsen et al., "Atmospheric chemistry of $CF_3CF=CH_2$. Kinetics and mechanisms of gas-phase reactions withCI atoms, OH radicals, and $O_3$," *Science Direct*, Chemical Physics Letters 439 (2007) pp. 18-22 (www.sciencedirect.com) US.
*ANSI/ASHRAE Standard 34-2007 Designation and Safety Classification of Refrigerants, 2007.*
*BSR/ASHRAE Addendum z zu ANSI-ASHRAE Standard 34-2007, Public Review Draft*, Sep. 2008.
M Spatz et al., "HFO-1234yf Low GWP Refrigerant," Presentation given at SAE 2008 Alternate Refrigerant Systems Symposium, Scottsdale (AZ), (Jun. 10-12, 2008) U.S.
V. I. Orkin et al., Rate Constants for the Reactions of OH with HFC-245cb ($CH_3$ CL Fluoroalkenes ($CH_2$ $CHCF_3$, $CH_2$ $CFCF_3$, $CF_2$ $CFCF_3$ and $CF_2$ $CF_2$, *J. Phys Chem. A*, vol. 101. pp. 9118-9124 (1997) US.
Wikipedia (the free encyclopedia) entry of Jul. 14, 2010, "HVAC, Background, heating, Ventilating, Air conditioning, Energy Efficiency, HVAC Industry and Standards," http://en.wikipedia.org/wiki/HVAC; and of collection of patent applications disclosing HVAC systems in automobiles.
Proposal for the Regulation of the European Parliament and of the Council on certain fluorinated greenhouse gases—Aug. 11, 2003.
Orkin et al., "Photochemistry of Bromine—containing Fluorinated Akenes; Reactivity toward OH and UV Spectra," J. Phys. Chem. A 2002, vol. 106, pp. 10195-10199 US.
Calorix Heat Pumps Ltd., "Energy Efficient Hot Water Heating," booklet, 4 pages. US.
Mitsubishi Electric, "Water Heating Units," (leaflet), (4 pages) GB.
Ivt Heat Pumps, "Greenline," (leaflet), (2 pages) SE.
Conergy, "Conergy Heat Pump: the Clever Choice for Hot Water," (leaflet), (2 pages) AU.
Dimplex, "Hot watr heat pump with sheet steel casing, air duct connection and additional heat exchanger," Data Sheet (1 page) DE.
Honeywell International Inc. "Guide to Alternative Refrigerants," (leaflet), (2 pages) US.

M Tekeuchi et al., "An Environmentally Friendly, Highly Efficient, Lightweight Scroll Compressor (QS90) For Car Air Conditioners" *Mitsubishi Heavy Industries, Ltd. Technical Review*, vol. 45, No. 3, pp. 24-26 (Sep. 2008) US.
New Refrigerant Insulating System Technology, pp. 75-78 (Apr. 15, 1996).
The Properties of Gases and Liquids, Poling et al, 2001, excerpts from chapters 2, 3, 4, 6 and 7.
Discussion on Modelling of Properties.
Fundamental Equation of State for 2,3,3,3-Tetrafluoropropene (HFO-1234yf) Ryo Akasaka et al. (HFO-1234yf Property Sheet).
Opposition 1—Arkema France (translation).
Opposition 1—Arkema further opposition documents (translation).
Opposition 2—Daikin Industris Ltd (translation).
Opposition 3—Asahi Glass Company Ltd.
Opposition 4—Daimler AG.
Opposition 5—ACEA European Automobile Manufactures Association.
Opposition 6—Anonymous.
Opposition 7—Bayerische Motoren Werke AG (translation).
Opposition 8—Mexichem Amanco Holdings SA.
Opposition 9—Solvay Fluor GmbH.
Observation 10—Potter Clarkson LLP, Third Party Observations to EP Patent Appl. No. 05744161.0, filed by lnneos Fluor Limited, Feb. 26, 2009. EP.
Observation 11—Anonymous—Filed by Arnason/Faktor, Intellectual Property Consulting, Reykjavik, Iceland, Dec. 9, 2008. IE.
Observation 12—Anonymous—Filed by Dr. Modiano & Associates, Milano, Feb. 26, 2009. IT.
Tarrant, et al., "Free Radical Additions Involving Fluorine Compounds. IV. The Addition of Dibromodifluoromethane to Some Fluoro06letins," J. Am. Chern Soc., 77,2783-2786 (1955).
Kunshenko, B. V. et al., "Reaction of Organic Compounds with SF4-HF-Halogenating System VII. Reactions of Oletins with the SF4-HF-CI2(Br2) System," Odessa DM Polytechnicallnstitute, Institute of Organic Chemistry, Academy of Sciences c the Ukraine, Kiev., Translated from Zhuranl Organicheskoi Khimii, 28(4), 672-80 (1982), Original article submitted Aug. 24,1989.
Additional Non-Patent Literature Documents Cited in U.S. Appl. No. 11/475,605 and Divisionals Thereof.
Database WPI Section Ch, Week 199221 Derwent Publications Ltd., London, GB; Class E16, AN 1992-172539.
Additional Non-Patent Literature Documents Cited in U.S. Appl. Nos. 10/837,526; 11/119,053; 12/198,411.
Written Opinion of International Search Authority for PCT/US2005/ 14874.
Albert W. Noyes, Editor, the Journal of the American Chemical Society, vol. LXXVII; Apr.-Jun. 1955 pp. 3149-3151. US.
Additional Non-Patent Literature Documents Cited in U.S. Appl. No. 11/474,887 and Divisionals and Continuation Thereof.
Jan H. Schutt, Polyurethane Foam Industry Prepares for 'Zero ODP', Plastics Technology—Internet article (http://www.plasticstechnology.com/articles/199911 fa3.html).
Perry Romanowski, "Polyurethane, How Plastics Are Made," Gale Edit, Volumes-Polyurethane. US.
Additional Non-Patent Literature Documents Cited in Parent U.S. Appl. Nos. 10/695,121 and 11/,385,259.
International Search Report for PCT/US04/35132 (corresponding U.S. Appl. No. 11/385,259).
Observation 13—Anonymous—Anonymous—Filed by Dr. Modiano & Associates, Milano, Apr. 2, 2009. IT.
English Translation of Official Action in Connection With Corresponding Japanese Patent Application No. 2004-547148.
Response to Japanese office action (not translated) and English language translation of claims as amended.
English Translation of JP Anonymous Submission of Prior Art References to Opposition to JP Application No. 2004-547148, dated Jun. 8, 2010.
Notice of Allowance in JP Application No. 2004-547148 (not translated) and allowed claims.
Reexamination Request—451 Patent.
Reexamination Request—805 Patent.

Additional Non-Patent Literature Documents Cited in U.S. Appl. No. 10/694,273.
Saunders and Frisch, "Polyurethanes Chemistry & Technology," vol. XVI, Part I and Part II Technology, John Wiley and Sons, New York, NY (1962), pp. 193-201 and 219-223. US.
Downing, Ralph C., "Fluorocarbon Refrigerants Handbook," Prentice Hall, Excepts from Chapter 3 and Chapter 16. US.
Additional Non-Patent Literature Documents Cited in U.S. Appl. No. 10/837,525 or 11/847,192.
Haszeldine, R. N. et al., "Free-radical Additions to Unsaturated Systems. Part XVII. Reaction of Trifluoroiodomethane with Mixtures of Ethylene and Vinyl Fluoride and of Ethylene and Propene," J. Chern. Soc., Section C, Organic (3), pp. 414-421 (1970).
Henne et al., "Fluorinated Derivatives of Propane and Propylene VI," J. Am. Chern. Soc., 68, pp. 496-497 (1946).
Kimura, et al., "Poly(ethylene glycols) and poly(ethylene glycol)-grafted copolymers are extraordinary catalysts for dehydrohalogenation under two-phase and three-phase conditions," J. Org. Chern., 48,195-0198 (1983).
Knunyants I. L. et al., "Reactions of Fluoro Olefins Communication 13, Catalytic DJ Hydrogenation of Perfluoro Oletins," Bulletin of the Academy of Sciences of the USSR, pp. 1312-1317.
EPO Communication in EP Application No. 08011766.6, Filed: Oct. 25, 2004, Applicant: Honeywell International Inc., Re: Third Party Observations filed Feb. 18, 2011 by Potter Clarkson LLP on behalf of anonymous third party. (EP).
Patent Owner's Response to the First Office Action Mailed Dec. 22, 2010, filed Mar. 21, 2011. (in In re Reexamination Control No. 95/000,576, Filed Oct. 5, 2010 for U.S. Patent No. 7,279,451).
Declaration of Rajiv R. Singh filed Mar. 21, 2011. (in In re Reexamination Control No. 95/000,576, Filed Oct. 5, 2010 for U.S. Patent No. 7,279,451).
Exhibit A—Rajiv Ratna Singh-U.S. Patents, (as attached to Declarationof Rajiv Ratna Sing, filed Mar. 21, 2011 in Patent Owner's Response to the First Office Action dated Dec. 22, 2010 in In re Reexamination Control No. 95/000,576, Filed Oct. 5, 2010 for U.S. Patent No. 7,279,451.)
Exhibit B—Rule 132 Declaration of George Rusch, dated Oct. 15, 2007 and Rule 132 Declaration of George Rusch dated Apr. 25, 2007 (as attached to Declaration of Rajiv Ratna Singh, filed Mar. 21, 2011 in Patent Owner's Response to the First Office Action dated Dec. 22, 2010 in In re Reexamination Control No. 95/000,576, Filed Oct. 5, 2010 for U.S. Patent No. 7,279,451.)
Exhibit C—European Centre fro Ecotoxicology and Toxicology of Chemical (ECETOC), "Toxcity of Possible Impurities and By-products in Fluorocarbon Products," Technical Report No. 103, (pp. 1 to 186), ISSN-0733-8072-103, Dec. 2008, Brussels, BE.
Exhibit D—Translationof JP Patent Application H4-110388, published Apr. 10, 1992 ("Inagaki").
Exhibit E—Denis Clodic, "Automobiel Air-Conditioning: Environmental Stakes and Future Technical Options," Journal of Cold and Air-conditioning, May 2008, original and certified translation, pp. 47-52. FR.
Exhibit F—Natasha Alperowicz, "Arkema Beefs UpChemicals; Eyes Acquisition of Acrylics Assets," Chemical Week, Nov. 17, 2008, p. 19.
Exhibit G—Industry Presentation, MAC Summit 2008, 1234yfOEM Group, "Update: 1234yf as a replacement for R134a," pp. 1-20).
Exhibit H—Paul Weissler, Ed., "EPA presses for fast switch to A/C refrigerant R-1234yf," Automotive Engineering International Online, Apr. 7, 2009, http://www.sae.org/mags/aei/6137.
Exhibit I—"GM First to Market Greenhouse Gas-Friendly Air Conditioning Refrigerant in U.S.," Jul. 23, 2010, online article at www.gm.com/corporate/responsibility/environment/news/2010/air_conditioning_refrigerant. US.
Exhibit J—Réne Müller, "First-Calss Air Conditioning," AutomobilKONSTRUKTION, Feb. 2009.
Exhibit K—"SAE Endorses Honeywell Refrigerant," Refrigeration and Air Conditioning Magazine (RAC), Jan. 2009.
Exhibit L—"EPA Approves New Coolant for Car Air Conditioning Systems/Better climate protection without harming the ozone layer," EPA: United States Environmental Protection Agency, Release date: Feb. 28, 2011.

* cited by examiner

COMPOSITIONS CONTAINING FLUORINE SUBSTITUTED OLEFINS

RELATED APPLICATIONS

The present application is related to and claims the priority benefit of each of the following U.S. Patent Applications: U.S. application Ser. No. 10/837,525, filed Apr. 29, 2004 (now U.S. Pat. No. 7,279,451), which in turn is a continuation-in-part of each of U.S. application Nos. 10/694,273 (now U.S. Pat. No. 7,534,366) and 10/694,272 (now U.S. Pat. No. 7,230,463), each of which was filed Oct. 27, 2003, and each of which in turn is related to and claims the priority benefit of U.S. Provisional Application Nos. 60/421,263, and 60/421,435, each of which was filed on Oct. 25, 2002.

FIELD OF THE INVENTION

This invention relates to compositions having utility in numerous applications, including particularly refrigeration systems, and to methods and systems utilizing such compositions. In preferred aspects, the present invention is directed to refrigerant compositions comprising at least one multi-fluorinated olefin of the present invention.

BACKGROUND OF THE INVENTION

Fluorocarbon based fluids have found widespread use in many commercial and industrial applications. For example, fluorocarbon based fluids are frequently used as a working fluid in systems such as air conditioning, heat pump and refrigeration applications. The vapor compression cycle is one of the most commonly used type methods to accomplish cooling or heating in a refrigeration system. The vapor compression cycle usually involves the phase change of the refrigerant from the liquid to the vapor phase through heat absorption at a relatively low pressure and then from the vapor to the liquid phase through heat removal at a relatively low pressure and temperature, compressing the vapor to a relatively elevated pressure, condensing the vapor to the liquid phase through heat removal at this relatively elevated pressure and temperature, and then reducing the pressure to start the cycle over again.

While the primary purpose of refrigeration is to remove heat from an object or other fluid at a relatively low temperature, the primary purpose of a heat pump is to add heat at a higher temperature relative to the environment.

Certain fluorocarbons have been a preferred component in many heat exchange fluids, such as refrigerants, for many years in many applications. For, example, fluoroalkanes, such as chlorofluoromethane and chlorofluoroethane derivatives, have gained widespread use as refrigerants in applications including air conditioning and heat pump applications owing to their unique combination of chemical and physical properties. Many of the refrigerants commonly utilized in vapor compression systems are either single components fluids or azeotropic mixtures.

Concern has increased in recent years about potential damage to the earth's atmosphere and climate, and certain chlorine-based compounds have been identified as particularly problematic in this regard. The use of chlorine-containing compositions (such as chlorofluorocarbons (CFCs), hydrochlorofluorocarbons (HCFCs) and the like) as refrigerants in air-conditioning and refrigeration systems has become disfavored because of the ozone-depleting properties associated with many of such compounds. There has thus been an increasing need for new fluorocarbon and hydrofluorocarbon compounds and compositions that offer alternatives for refrigeration and heat pump applications. For example, it has become desirable to retrofit chlorine-containing refrigeration systems by replacing chlorine-containing refrigerants with non-chlorine-containing refrigerant compounds that will not deplete the ozone layer, such as hydrofluorocarbons (HFCs).

It is generally considered important, however, that any potential substitute refrigerant must also possess those properties present in many of the most widely used fluids, such as excellent heat transfer properties, chemical stability, low- or no-toxicity, non-flammability and lubricant compatibility, among others.

Applicants have come to appreciate that lubricant compatibility is of particular importance in many of applications. More particularly, it is highly desirably for refrigeration fluids to be compatible with the lubricant utilized in the compressor unit, used in most refrigeration systems. Unfortunately, many non-chlorine-containing refrigeration fluids, including HFCs, are relatively insoluble and/or immiscible in the types of lubricants used traditionally with CFC's and HFCs, including, for example, mineral oils, alkylbenzenes or poly(alpha-olefins). In order for a refrigeration fluid-lubricant combination to work at a desirable level of efficiently within a compression refrigeration, air-conditioning and/or heat pump system, the lubricant should be sufficiently soluble in the refrigeration liquid over a wide range of operating temperatures. Such solubility lowers the viscosity of the lubricant and allows it to flow more easily throughout the system. In the absence of such solubility, lubricants tend to become lodged in the coils of the evaporator of the refrigeration, air-conditioning or heat pump system, as well as other parts of the system, and thus reduce the system efficiency.

With regard to efficiency in use, it is important to note that a loss in refrigerant thermodynamic performance or energy efficiency may have secondary environmental impacts through increased fossil fuel usage arising from an increased demand for electrical energy.

Furthermore, it is generally considered desirably for CFC refrigerant substitutes to be effective without major engineering changes to conventional vapor compression technology currently used with CFC refrigerants.

Flammability is another important property for many applications. That is, it is considered either important or essential in many applications, including particularly in heat transfer applications, to use compositions, which are non-flammable. Thus, it is frequently beneficial to use in such compositions compounds, which are nonflammable. As used herein, the term "nonflammable" refers to compounds or compositions, which are determined to be nonflammable as determined in accordance with ASTM standard E-681, dated 2002, which is incorporated herein by reference. Unfortunately, many HFCs, which might otherwise be desirable for used in refrigerant compositions are not nonflammable. For example, the fluoroalkane difluoroethane (HFC-152a) and the fluoroalkene 1,1,1-trifluoropropene (HFO-1243zf) are each flammable and therefore not viable for use in many applications.

Higher fluoroalkenes, that is fluorine-substituted alkenes having at least five carbon atoms, have been suggested for use as refrigerants. U.S. Pat. No. 4,788,352—Smutny is directed to production of fluorinated $C_5$ to $C_8$ compounds having at least some degree of unsaturation. The Smutny patent identifies such higher olefins as being known to have utility as refrigerants, pesticides, dielectric fluids, heat transfer fluids, solvents, and intermediates in various chemical reactions. (See column 1, lines 11-22).

While the fluorinated olefins described in Smutny may have some level of effectiveness in heat transfer applications, it is believed that such compounds may also have certain disadvantages. For example, some of these compounds may tend to attack substrates, particularly general-purpose plastics such as acrylic resins and ABS resins. Furthermore, the higher olefinic compounds described in Smutny may also be undesirable in certain applications because of the potential level of toxicity of such compounds which may arise as a result of pesticide activity noted in Smutny. Also, such compounds may have a boiling point, which is too high to make them useful as a refrigerant in certain applications.

Bromofluoromethane and bromochlorofluoromethane derivatives, particularly bromotrifluoromethane (Halon 1301) and bromochlorodifluoromethane (Halon 1211) have gained widespread use as fire extinguishing agents in enclosed areas such as airplane cabins and computer rooms. However, the use of various halons is being phased out due to their high ozone depletion. Moreover, as halons are frequently used in areas where humans are present, suitable replacements must also be safe to humans at concentrations necessary to suppress or extinguish fire.

Applicants have thus come to appreciate a need for compositions, and particularly heat transfer compositions, fire extinguishing/suppression compositions, blowing agents, solvent compositions, and compatabilizing agents, that are potentially useful in numerous applications, including vapor compression heating and cooling systems and methods, while avoiding one or more of the disadvantages noted above.

SUMMARY

Applicants have found that the above-noted need, and other needs, can be satisfied by compositions comprising one or more C3 or C4 fluoroalkenes, preferably compounds having Formula I as follows:

$$XCF_zR_{3-z} \quad (I)$$

where X is a $C_2$ or a $C_3$ unsaturated, substituted or unsubstituted, alkyl radical, each R is independently Cl, F, Br, I or H, and z is 1 to 3. Highly preferred among the compounds of Formula I are the cis- and trans-isomers of 1,3,3,3-tetrafluoropropene (HFO-1234ze)

The present invention provides also methods and systems which utilize the compositions of the present invention, including methods and systems for heat transfer, foam blowing, solvating, flavor and fragrance extraction and/or delivery, and aerosol generation.

DETAILED DESCRIPTION OF PREFERRED EMBODIMENTS

The Compositions

The present invention is directed to compositions comprising at least one fluoroalkene containing from 3 to 4 carbon atoms, preferably three carbon atoms, and at least one carbon-carbon double bond. The fluoroalkene compounds of the present invention are sometimes referred to herein for the purpose of convenience as hydrofluoro-olefins or "HFOs" if they contain at least one hydrogen. Although it is contemplated that the HFOs of the present invention may contain two carbon—carbon double bonds, such compounds at the present time are not considered to be preferred.

As mentioned above, the present compositions comprise one or more compounds in accordance with Formula I. In preferred embodiments, the compositions include compounds of Formula II below:

where each R is independently Cl, F, Br, I or H
R' is $(CR_2)_nY$,
Y is $CRF_2$
and n is 0 or 1.

In highly preferred embodiments, Y is $CF_3$, n is 0 and at least one of the remaining Rs is F.

Applicants believe that, in general, the compounds of the above identified Formulas I and II are generally effective and exhibit utility in refrigerant compositions, blowing agent compositions, compatibilizers, aerosols, propellants, fragrances, flavor formulations, and solvent compositions of the present invention. However, applicants have surprisingly and unexpectedly found that certain of the compounds having a structure in accordance with the formulas described above exhibit a highly desirable low level of toxicity compared to other of such compounds. As can be readily appreciated, this discovery is of potentially enormous advantage and benefit for the formulation of not only refrigerant compositions, but also any and all compositions, which would otherwise contain relatively toxic compounds satisfying the formulas described above. More particularly, applicants believe that a relatively low toxicity level is associated with compounds of Formula II, preferably wherein Y is $CF_3$, wherein at least one R on the unsaturated terminal carbon is H, and at least one of the remaining Rs is F. Applicants believe also that all structural, geometric and stereoisomers of such compounds are effective and of beneficially low toxicity.

In highly preferred embodiments, especially embodiments comprising the low toxicity compounds described above, n is zero. In certain highly preferred embodiments the compositions of the present invention comprise one or more tetrafluoropropenes. The term "HFO-1234" is used herein to refer to all tetrafluoropropenes. Among the tetrafluoropropenes, both cis- and trans-1,3,3,3-tetrafluoropropene (HFO-1234ze) are particularly preferred. The term HFO-1234ze is used herein generically to refer to 1,3,3,3-tetrafluoropropene, independent of whether it is the cis- or trans-form. The terms "cisHFO-1234ze" and "transHFO-1234ze" are used herein to describe the cis- and trans-forms of 1,3,3,3-tetrafluoropropene respectively. The term "HFO-1234ze" therefore includes within its scope cisHFO-1234ze, transHFO-1234ze, and all combinations and mixtures of these.

Although the properties of cisHFO-1234ze and transHFO-1234ze differ in at least some respects, it is contemplated that each of these compounds is adaptable for use, either alone or together with other compounds including its stereoisomer, in connection with each of the applications, methods and systems described herein. For example, while transHFO-1234ze may be preferred for use in certain refrigeration systems because of its relatively low boiling point (−19° C.), it is nevertheless contemplated that cisHFO-1234ze, with a boiling point of +9° C., also has utility in certain refrigeration systems of the present invention. Accordingly, it is to be understood that the terms "HFO-1234ze" and 1,3,3,3-tetrafluoropropene refer to both stereo isomers, and the use of this term is intended to indicate that each of the cis-and trans-forms applies and/or is useful for the stated purpose unless otherwise indicated.

HFO-1234 compounds are known materials and are listed in Chemical Abstracts databases. The production of fluoropropenes such as $CF_3CH=CH_2$ by catalytic vapor phase fluorination of various saturated and unsaturated halogen-containing $C_3$ compounds is described in U.S. Pat. Nos. 2,889,379; 4,798,818 and 4,465,786, each of which is incorporated herein by reference. EP 974,571, also incorporated herein by reference, discloses the preparation of 1,1,1,3-tetrafluoropropene by contacting 1,1,1,3,3-pentafluoropropane (HFC-245fa) in the vapor phase with a chromium-based catalyst at elevated temperature, or in the liquid phase with an alcoholic solution of KOH, NaOH, $Ca(OH)_2$ or $Mg(OH)_2$. In addition, methods for producing compounds in accordance with the present invention are described generally in connection with pending United States patent application entitled "Process for Producing Fluoropropenes" bearing attorney docket number (H0003789 (26267)), which is also incorporated herein by reference.

The present compositions, particularly those comprising HFO-1234ze, are believed to possess properties that are advantageous for a number of important reasons. For example, applicants believe, based at least in part on mathematical modeling, that the fluoroolefins of the present invention will not have a substantial negative affect on atmospheric chemistry, being negligible contributors to ozone depletion in comparison to some other halogenated species. The preferred compositions of the present invention thus have the advantage of not contributing substantially to ozone depletion. The preferred compositions also do not contribute substantially to global warming compared to many of the hydrofluoroalkanes presently in use.

In certain preferred forms, compositions of the present invention have a Global Warming Potential (GWP) of not greater than about 1000, more preferably not greater than about 500, and even more preferably not greater than about 150. In certain embodiments, the GWP of the present compositions is not greater than about 100 and even more preferably not greater than about 75. As used herein, "GWP" is measured relative to that of carbon dioxide and over a 100-year time horizon, as defined in "The Scientific Assessment of Ozone Depletion, 2002, a report of the World Meteorological Association's Global Ozone Research and Monitoring Project," which is incorporated herein by reference.

In certain preferred forms, the present compositions also preferably have an Ozone Depletion Potential (ODP) of not greater than 0.05, more preferably not greater than 0.02 and even more preferably about zero. As used herein, "ODP" is as defined in "The Scientific Assessment of Ozone Depletion, 2002, A report of the World Meteorological Association's Global Ozone Research and Monitoring Project," which is incorporated herein by reference.

The amount of the Formula I compounds, particularly HFO-1234, contained in the present compositions can vary widely, depending the particular application, and compositions containing more than trace amounts and less than 100% of the compound are within broad scope of the present invention. Moreover, the compositions of the present invention can be azeotropic, azeotrope-like or non-azeotropic. In preferred embodiments, the present compositions comprise HFO-1234, preferably HFO-1234ze, in amounts from about 5% by weight to about 99% by weight, and even more preferably from about 5% to about 95%. Many additional compounds may be included in the present compositions, and the presence of all such compounds is within the broad scope of the invention. In certain preferred embodiments, the present compositions include, in addition to HFO-1234ze, one or more of the following:

Difluoromethane (HFC-32)
Pentafluoroethane (HFC-125)
1,1,2,2-tetrafluoroethane (HFC-134)
1,1,1,2-Tetrafluoroethane (HFC-134a)
Difluoroethane (HFC-152a)
1,1,1,2,3,3,3-Heptafluoropropane (HFC-227ea)
1,1,1,3,3,3-hexafluoropropane (HFC-236fa)
1,1,1,3,3-pentafluoropropane (HFC-245fa)
1,1,1,3,3-pentafluorobutane (HFC-365mfc)
water
$CO_2$ The relative amount of any of the above noted components, as well as any additional components which may be included in present compositions, can vary widely within the general broad scope of the present invention according to the particular application for the composition, and all such relative amounts are considered to be within the scope hereof.

Heat Transfer Compositions

Although it is contemplated that the compositions of the present invention may include the compounds of the present invention in widely ranging amounts, it is generally preferred that refrigerant compositions of the present invention comprise compound(s) in accordance with Formula I, more preferably in accordance with Formula II, and even more preferably HFO-1234ze, in an amount that is at least about 50% by weight, and even more preferably at least about 70% by weight, of the composition. In many embodiments, it is preferred that the heat transfer compositions of the present invention comprise transHFO-1234ze. In certain preferred embodiments, the heat transfer compositions of the present invention comprise a combination of cisHFO-1234ze and transHFO1234ze in a cis:trans weight ratio of from about 1:99 to about 10:99, more preferably from about 1:99 to about 5:95, and even more preferably from about 1:99 to about 3:97.

The compositions of the present invention may include other components for the purpose of enhancing or providing certain functionality to the composition, or in some cases to reduce the cost of the composition. For example, refrigerant compositions according to the present invention, especially those used in vapor compression systems, include a lubricant, generally in amounts of from about 30 to about 50 percent by weight of the composition. Furthermore, the present compositions may also include a compatibilizer, such as propane, for the purpose of aiding compatibility and/or solubility of the lubricant. Such compatibilizers, including propane, butanes and pentanes, are preferably present in amounts of from about 0.5 to about 5 percent by weight of the composition. Combinations of surfactants and solubilizing agents may also be added to the present compositions to aid oil solubility, as disclosed by U.S. Pat. No. 6,516,837, the disclosure of which is incorporated by reference. Commonly used refrigeration lubricants such as Polyol Esters (POEs) and Poly Alkylene Glycols (PAGs), silicone oil, mineral oil, alkyl benzenes (ABs) and poly(alpha-olefin) (PAO) that are used in refrigeration machinery with hydrofluorocarbon (HFC) refrigerants may be used with the refrigerant compositions of the present invention.

Many existing refrigeration systems are currently adapted for use in connection with existing refrigerants, and the compositions of the present invention are believed to be adaptable for use in many of such systems, either with or without system modification. In many applications the compositions of the present invention may provide an advantage as a replacement in systems, which are currently based on refrigerants having a relatively high capacity. Furthermore, in embodiments where it is desired to use a lower capacity refrigerant composition of the present invention, for reasons of cost for example, to replace a refrigerant of higher capacity, such embodiments of the present compositions provide a potential advantage. Thus, It is preferred in certain embodiments to use compositions of the present invention, particularly compositions comprising a substantial proportion of, and in some embodiments consisting essentially of transHFO-1234ze, as a replacement for existing refrigerants, such as HFC-134a. In certain applications, the refrigerants of the present invention potentially permit the beneficial use of larger displacement compressors, thereby resulting in better energy efficiency than other refrigerants, such as HFC-134a. Therefore the refrigerant compositions of the present invention, particularly compositions comprising transHFP-1234ze, provide the possibility of achieving a competitive advantage on an energy basis for refrigerant replacement applications.

It is contemplated that the compositions of the present, including particularly those comprising HFO-1234ze, also have advantage (either in original systems or when used as a replacement for refrigerants such as R-12 and R-500), in chillers typically used in connection with commercial air conditioning systems. In certain of such embodiments it is preferred to including in the present HFO-1234ze compositions from about 0.5 to about 5% of a flammability suppressant, such as CF3I.

The present methods, systems and compositions are thus adaptable for use in connection with automotive air conditioning systems and devices, commercial refrigeration systems and devices, chillers, residential refrigerator and freezers, general air conditioning systems, heat pumps, and the like.

Blowing Agents, Foams and Foamable Compositions

Blowing agents may also comprise or constitute one or more of the present compositions. As mentioned above, the compositions of the present invention may include the compounds of the present invention in widely ranging amounts. It is generally preferred, however, that for preferred compositions for use as blowing agents in accordance with the present invention, compound(s) in accordance with Formula I, and even more preferably Formula II, are present in an amount that is at least about 5% by weight, and even more preferably at least about 15% by weight, of the composition. In certain preferred embodiments, the blowing agent compositions of the present invention and include, in addition to HFO-1234 (preferably HFO-1234ze) one or more of the following components as a co-blowing agent, filler, vapor pressure modifier, or for any other purpose:

Difluoromethane (HFC-32)
Pentafluoroethane (HFC-125)
1,1,2,2-tetrafluoroethane (HFC-134)
1,1,1,2-Tetrafluoroethane (HFC-134a)
Difluoroethane (HFC-152a)
1,1,1,2,3,3,3-Heptafluoropropane (HFC-227ea)
1,1,1,3,3,3-hexafluoropropane (HFC-236fa)
1,1,1,3,3-pentafluoropropane (HFC-245fa)
1,1,1,3,3-pentafluorobutane (HFC-365mfc)
water
$CO_2$ it is contemplated that the blowing agent compositions of the present invention may comprise cisHFO-1234ze, transHFO1234ze or combinations thereof. In certain preferred embodiments, the blowing agent composition of the present invention comprise his a combination of cisHFO-1234ze and transHFO1234ze in a cis:trans weight ratio of from about 1:99 to about 10:99, and even more preferably from about 1:99 to about 5:95.

In other embodiments, the invention provides foamable compositions, and preferably polyurethane, polyisocyanurate and extruded thermoplastic foam compositions, prepared using the compositions of the present invention. In such foam embodiments, one or more of the present compositions are included as or part of a blowing agent in a foamable composition, which composition preferably includes one or more additional components capable of reacting and/or foaming under the proper conditions to form a foam or cellular structure, as is well known in the art. The invention also relates to foam, and preferably closed cell foam, prepared from a polymer foam formulation containing a blowing agent comprising the compositions of the invention. In yet other embodiments, the invention provides foamable compositions comprising thermoplastic or polyolefin foams, such as polystyrene (PS), polyethylene (PE), polypropylene (PP) and polyethyleneterpthalate (PET) foams, preferably low-density foams.

In certain preferred embodiments, dispersing agents, cell stabilizers, surfactants and other additives may also be incorporated into the blowing agent compositions of the present invention. Surfactants are optionally but preferably added to serve as cell stabilizers. Some representative materials are sold under the names of DC-193, B-8404, and L-5340 which are, generally, polysiloxane polyoxyalkylene block co-polymers such as those disclosed in U.S. Pat. Nos. 2,834,748, 2,917,480, and 2,846,458, each of which is incorporated herein by reference. Other optional additives for the blowing agent mixture may include flame retardants such as tri(2-chloroethyl)phosphate, tri(2-chloropropyl)phosphate, tri(2,3-dibromopropyl)-phosphate, tri(1,3-dichloropropyl) phosphate, diammonium phosphate, various halogenated aromatic compounds, antimony oxide, aluminum trihydrate, polyvinyl chloride, and the like.

Propellant and Aerosol Compositions

In another aspect, the present invention provides propellant compositions comprising or consisting essentially of a composition of the present invention, such propellant composition preferably being a sprayable composition. The propellant compositions of the present invention preferably comprise a material to be sprayed and a propellant comprising, consisting essentially of, or consisting of a composition in accordance with the present invention. Inert ingredients, solvents, and other materials may also be present in the sprayable mixture. Preferably, the sprayable composition is an aerosol. Suitable materials to be sprayed include, without limitation, cosmetic materials such as deodorants, perfumes, hair sprays, cleansers, and polishing agents as well as medicinal materials such as anti-asthma components, anti-halitosis components and any other medication or the like, including preferably any other medicament or agent intended to be inhaled. The medicament or other therapeutic agent is preferably present in the composition in a therapeutic amount, with a substantial portion of the balance of the composition comprising a compound of Formula I of the present invention, preferably HFO-1234, and even more preferably HFO-1234ze.

Aerosol products for industrial, consumer or medical use typically contain one or more propellants along with one or more active ingredients, inert ingredients or solvents. The propellant provides the force that expels the product in aerosolized form. While some aerosol products are propelled with compressed gases like carbon dioxide, nitrogen, nitrous oxide and even air, most commercial aerosols use liquefied gas propellants. The most commonly used liquefied gas propellants are hydrocarbons such as butane, isobutane, and propane. Dimethyl ether and HFC-152a (1,1-difluoroethane) are also used, either alone or in blends with the hydrocarbon propellants. Unfortunately, all of these liquefied gas propellants are highly flammable and their incorporation into aerosol formulations will often result in flammable aerosol products.

Applicants have come to appreciate the continuing need for nonflammable, liquefied gas propellants with which to formulate aerosol products. The present invention provides compositions of the present invention, particularly and preferably compositions comprising HFO-1234, and even more preferably HFO-1234ze, for use in certain industrial aerosol products, including for example spray cleaners, lubricants, and the like, and in medicinal aerosols, including for example to deliver medications to the lungs or mucosal membranes. Examples of this includes metered dose inhalers (MDIs) for the treatment of asthma and other chronic obstructive pulmonary diseases and for delivery of medicaments to accessible mucous membranes or intranasally. The present invention thus includes methods for treating ailments, diseases and similar health related problems of an organism (such as a human or animal) comprising applying a composition of the present invention containing a medicament or other therapeutic component to the organism in need of treatment. In certain preferred embodiments, the step of applying the present composition comprises providing a MDI containing the composition of the present invention (for example, introducing the composition into the MDI) and then discharging the present composition from the MDI.

The compositions of the present invention, particularly compositions comprising or consisting essentially of HFO-1234ze, are capable of providing nonflammable, liquefied gas propellant and aerosols that do not contribute substantially to global warming. The present compositions can be used to formulate a variety of industrial aerosols or other sprayable compositions such as contact cleaners, dusters, lubricant sprays, and the like, and consumer aerosols such as personal care products, household products and automotive products. HFO-1234ze is particularly preferred for use as an important component of propellant compositions for in medicinal aerosols such as metered dose inhalers. The medicinal aerosol and/or propellant and/or sprayable compositions of the present invention in many applications include, in addition to compound of formula (I) or (II) (preferably HFO-1234ze), a medicament such as a beta-agonist, a corticosteroid or other medicament, and, optionally, other ingredients, such as surfactants, solvents, other propellants, flavorants and other excipients. The compositions of the present invention, unlike many compositions previously used in these applications, have good environmental properties and are not considered to be potential contributors to global warming. The present compositions therefore provide in certain preferred embodiments substantially nonflammable, liquefied gas propellants having very low Global Warming potentials.

Flavorants and Fragrances

The compositions of the present invention also provide advantage when used as part of, and in particular as a carrier for, flavor formulations and fragrance formulations. The suitability of the present compositions for this purpose is demonstrated by a test procedure in which 0.39 grams of Jasmone were put into a heavy walled glass tube. 1.73 grams of R-1234ze were added to the glass tube. The tube was then frozen and sealed. Upon thawing the tube, it was found that the mixture had one liquid phase. The solution contained 20 wt. % Jasome and 80 wt. % R-1234ze, thus establishing its favorable use as a carrier or part of delivery system for flavor formulations, in aerosol and other formulations. It also establishes its potential as an extractant of fragrances, including from plant matter.

Methods and Systems

The compositions of the present invention are useful in connection with numerous methods and systems, including as heat transfer fluids in methods and systems for transferring heat, such as refrigerants used in refrigeration, air conditioning and heat pump systems. The present compositions are also advantageous for in use in systems and methods of generating aerosols, preferably comprising or consisting of the aerosol propellant in such systems and methods. Methods of forming foams and methods of extinguishing and suppressing fire are also included in certain aspects of the present invention. The present invention also provides in certain aspects methods of removing residue from articles in which the present compositions are used as solvent compositions in such methods and systems.

Heat Transfer Methods

The preferred heat transfer methods generally comprise providing a composition of the present invention and causing heat to be transferred to or from the composition changing the phase of the composition. For example, the present methods provide cooling by absorbing heat from a fluid or article, preferably by evaporating the present refrigerant composition in the vicinity of the body or fluid to be cooled to produce vapor comprising the present composition. Preferably the methods include the further step of compressing the refrigerant vapor, usually with a compressor or similar equipment to produce vapor of the present composition at a relatively elevated pressure. Generally, the step of compressing the vapor results in the addition of heat to the vapor, thus causing an increase in the temperature of the relatively high-pressure vapor. Preferably, the present methods include removing from this relatively high temperature, high pressure vapor at least a portion of the heat added by the evaporation and compression steps. The heat removal step preferably includes condensing the high temperature, high-pressure vapor while the vapor is in a relatively high-pressure condition to produce a relatively high-pressure liquid comprising a composition of the present invention. This relatively high-pressure liquid preferably then undergoes a nominally isoenthalpic reduction in pressure to produce a relatively low temperature, low-pressure liquid. In such embodiments, it is this reduced temperature refrigerant liquid which is then vaporized by heat transferred from the body or fluid to be cooled.

In another process embodiment of the invention, the compositions of the invention may be used in a method for producing heating which comprises condensing a refrigerant comprising the compositions in the vicinity of a liquid or body to be heated. Such methods, as mentioned hereinbefore, frequently are reverse cycles to the refrigeration cycle described above.

Foam Blowing Methods

One embodiment of the present invention relates to methods of forming foams, and preferably polyurethane and polyisocyanurate foams. The methods generally comprise providing a blowing agent composition of the present inventions, adding (directly or indirectly) the blowing agent composition to a foamable composition, and reacting the foamable composition under the conditions effective to form a foam or cellular structure, as is well known in the art. Any of the methods well known in the art, such as those described in "Polyurethanes Chemistry and Technology," Volumes I and II, Saunders and Frisch, 1962, John Wiley and Sons, New York, N.Y., which is incorporated herein by reference, may be used or adapted for use in accordance with the foam embodiments of the present invention. In general, such preferred methods comprise preparing polyurethane or polyisocyanurate foams by combining an isocyanate, a polyol or mixture of polyols, a blowing agent or mixture of blowing agents comprising one or more of the present compositions, and other materials such as catalysts, surfactants, and optionally, flame retardants, colorants, or other additives.

It is convenient in many applications to provide the components for polyurethane or polyisocyanurate foams in pre-blended formulations. Most typically, the foam formulation is pre-blended into two components. The isocyanate and optionally certain surfactants and blowing agents comprise the first component, commonly referred to as the "A" component. The polyol or polyol mixture, surfactant, catalysts, blowing agents, flame retardant, and other isocyanate reactive components comprise the second component, commonly referred to as the "B" component. Accordingly, polyurethane or polyisocyanurate foams are readily prepared by bringing together the A and B side components either by hand mix for small preparations and, preferably, machine mix techniques to form blocks, slabs, laminates, pour-in-place panels and other items, spray applied foams, froths, and the like. Optionally, other ingredients such as fire retardants, colorants, auxiliary blowing agents, and even other polyols can be added as a third stream to the mix head or reaction site. Most preferably, however, they are all incorporated into one B-component as described above.

It is also possible to produce thermoplastic foams using the compositions of the invention. For example, conventional polystyrene and polyethylene formulations may be combined with the compositions in a conventional manner to produce rigid foams.

Cleaning Methods

The present invention also provides methods of removing containments from a product, part, component, substrate, or any other article or portion thereof by applying to the article a composition of the present invention. For the purposes of convenience, the term "article" is used herein to refer to all such products, parts, components, substrates, and the like and is further intended to refer to any surface or portion thereof. Furthermore, the term "contaminant" is intended to refer to any unwanted material or substance present on the article, even if such substance is placed on the article intentionally. For example, in the manufacture of semiconductor devices it is common to deposit a photoresist material onto a substrate to form a mask for the etching operation and to subsequently remove the photoresist material from the substrate. The term "contaminant" as used herein is intended to cover and encompass such a photo resist material.

Preferred methods of the present invention comprise applying the present composition to the article. Although it is contemplated that numerous and varied cleaning techniques can employ the compositions of the present invention to good advantage, it is considered to be particularly advantageous to use the present compositions in connection with supercritical cleaning techniques. Supercritical cleaning is disclosed in U.S. Pat. No. 6,589,355, which is assigned to the assignee of the present invention and incorporated herein by reference. For supercritical cleaning applications, is preferred in certain embodiments to include in the present cleaning compositions, in addition to the HFO-1234 (preferably HFO-1234ze), one or more additional components, such as $CO_2$ and other additional components known for use in connection with supercritical cleaning applications. It may also be possible and desirable in certain embodiments to use the present cleaning compositions in connection with particular vapor degreasing and solvent cleaning methods.

Flammability Reduction Methods

According to certain other preferred embodiments, the present invention provides methods for reducing the flammability of fluids, said methods comprising adding a compound or composition of the present invention to said fluid. The flammability associated with any of a wide range of otherwise flammable fluids may be reduced according to the present invention. For example, the flammability associated with fluids such as ethylene oxide, flammable hydrofluorocarbons and hydrocarbons, including: HFC-152a, 1,1,1-trifluoroethane (HFC-143a), difluoromethane (HFC-32), propane, hexane, octane, and the like can be reduced according to the present invention. For the purposes of the present invention, a flammable fluid may be any fluid exhibiting flammability ranges in air as measured via any standard conventional test method, such as ASTM E-681, and the like.

Any suitable amounts of the present compounds or compositions may be added to reduce flammability of a fluid according to the present invention. As will be recognized by those of skill in the art, the amount added will depend, at least in part, on the degree to which the subject fluid is flammable and the degree to which it is desired to reduce the flammability thereof. In certain preferred embodiments, the amount of compound or composition added to the flammable fluid is effective to render the resulting fluid substantially non-flammable.

Flame Suppression Methods

The present invention further provides methods of suppressing a flame, said methods comprising contacting a flame with a fluid comprising a compound or composition of the present invention. Any suitable methods for contacting the flame with the present composition may be used. For example, a composition of the present invention may be sprayed, poured, and the like onto the flame, or at least a portion of the flame may be immersed in the composition. In light of the teachings herein, those of skill in the art will be readily able to adapt a variety of conventional apparatus and methods of flame suppression for use in the present invention.

Sterilization Methods

Many articles, devices and materials, particularly for use in the medical field, must be sterilized prior to use for the health and safety reasons, such as the health and safety of patients and hospital staff. The present invention provides methods of sterilizing comprising contacting the articles, devices or material to be sterilized with a compound or composition of the present invention comprising a compound of Formula I, preferably HFO-1234, and even more preferably HFO-1234ze, in combination with one or more sterilizing agents. While many sterilizing agents are known in the art and are considered to be adaptable for use in connection with the present invention, in certain preferred embodiments sterilizing agent comprises ethylene oxide, formaldehyde, hydrogen peroxide, chlorine dioxide, ozone and combinations of these. In certain embodiments, ethylene oxide is the preferred sterilizing agent. Those skilled in the art, in view of the teachings contained herein, will be able to readily determine the relative proportions of sterilizing agent and the present compound(s) to be used in connection with the present sterilizing compositions and methods, and all such ranges are within the broad scope hereof. As is known to those skilled in the art, certain sterilizing agents, such as ethylene oxide, are relatively flammable components, and the compound(s) in accordance with the present invention are included in the present compositions in amounts effective, together with other components present in the composition, to reduce the flammability of the sterilizing composition to acceptable levels.

The sterilization methods of the present invention may be either high or low-temperature sterilization of the present invention involves the use of a compound or composition of the present invention at a temperature of from about 250° F. to about 270° F., preferably in a substantially sealed chamber. The process can be completed usually in less than about 2 hours. However, some articles, such as plastic articles and electrical components, cannot withstand such high temperatures and require low-temperature sterilization. In low temperature sterilization methods, the article to be sterilized is exposed to a fluid comprising a composition of the present invention at a temperature of from about room temperature to about 200° F., more preferably at a temperature of from about room temperature to about 100° F.

The low-temperature sterilization of the present invention is preferably at least a two-step process performed in a substantially sealed, preferably air tight, chamber. In the first step (the sterilization step), the articles having been cleaned and wrapped in gas permeable bags are placed in the chamber. Air is then evacuated from the chamber by pulling a vacuum and perhaps by displacing the air with steam. In certain embodiments, it is preferable to inject steam into the chamber to achieve a relative humidity that ranges preferably from about 30% to about 70%. Such humidities may maximize the sterilizing effectiveness of the sterilant, which is introduced into the chamber after the desired relative humidity is achieved. After a period of time sufficient for the sterilant to permeate the wrapping and reach the interstices of the article, the sterilant and steam are evacuated from the chamber.

In the preferred second step of the process (the aeration step), the articles are aerated to remove sterilant residues. Removing such residues is particularly important in the case of toxic sterilants, although it is optional in those cases in which the substantially non-toxic compounds of the present invention are used. Typical aeration processes include air washes, continuous aeration, and a combination of the two. An air wash is a batch process and usually comprises evacuating the chamber for a relatively short period, for example, 12 minutes, and then introducing air at atmospheric pressure or higher into the chamber. This cycle is repeated any number of times until the desired removal of sterilant is achieved. Continuous aeration typically involves introducing air through an inlet at one side of the chamber and then drawing it out through an outlet on the other side of the chamber by applying a slight vacuum to the outlet. Frequently, the two approaches are combined. For example, a common approach involves performing air washes and then an aeration cycle.

EXAMPLES

The following examples are provided for the purpose of illustrating the present invention but without limiting the scope thereof.

Example 1

The coefficient of performance (COP) is a universally accepted measure of refrigerant performance, especially useful in representing the relative thermodynamic efficiency of a refrigerant in a specific heating or cooling cycle involving evaporation or condensation of the refrigerant. In refrigeration engineering, this term expresses the ratio of useful refrigeration to the energy applied by the compressor in compressing the vapor. The capacity of a refrigerant represents the amount of cooling or heating it provides and provides some measure of the capability of a compressor to pump quantities of heat for a given volumetric flow rate of refrigerant. In other words, given a specific compressor, a refrigerant with a higher capacity will deliver more cooling or heating power. One means for estimating COP of a refrigerant at specific operating conditions is from the thermodynamic properties of the refrigerant using standard refrigeration cycle analysis techniques (see for example, R. C. Downing, FLUOROCARBON REFRIGERANTS HANDBOOK, Chapter 3, Prentice-Hall, 1988).

A refrigeration/air conditioning cycle system is provided where the condenser temperature is about 150° F. and the evaporator temperature is about −35° F. under nominally isentropic compression with a compressor inlet temperature of about 50° F. COP is determined for several compositions of the present invention over a range of condenser and evaporator temperatures and reported in Table I below, based upon HFC-134a having a COP value of 1.00, a capacity value of 1.00 and a discharge temperature of 175° F.

TABLE I

| REFRIGERANT COMPOSITION | Relative COP | Relative CAPACITY | DISCHARGE TEMPERATURE (° F.) |
|---|---|---|---|
| HFO 1225ye | 1.02 | 0.76 | 158 |
| HFO trans-1234ze | 1.04 | 0.70 | 165 |
| HFO cis-1234ze | 1.13 | 0.36 | 155 |
| HFO 1234yf | 0.98 | 1.10 | 168 |

This example shows that certain of the preferred compounds for use with the present compositions each have a better energy efficiency than HFC-134a (1.02, 1.04 and 1.13 compared to 1.00) and the compressor using the present refrigerant compositions will produce discharge temperatures (158, 165 and 155 compared to 175), which is advantageous since such result will likely leading to reduced maintenance problems.

Example 2

The miscibility of HFO-1225ye and HFO-1234ze with various refrigeration lubricants is tested. The lubricants tested are mineral oil (C3), alkyl benzene (Zerol 150), ester oil (Mobil EAL 22 cc and Solest 120), polyalkylene glycol (PAG) oil (Goodwrench Refrigeration Oil for 134a systems), and a poly(alpha-olefin) oil (CP-6005-100). For each refrigerant/oil combination, three compositions are tested, namely 5, 20 and 50 weight percent of lubricant, with the balance of each being the compound of the present invention being tested The lubricant compositions are placed in heavy-walled glass tubes. The tubes are evacuated, the refrigerant compound in accordance with the present invention is added, and the tubes are then sealed. The tubes are then put into an air bath environmental chamber, the temperature of which is varied from about −50° C. to 70° C. At roughly 10° C. intervals, visual observations of the tube contents are made for the existence of one or more liquid phases. In a case where more than one liquid phase is observed, the mixture is reported to be immiscible. In a case where there is only one liquid phase observed, the mixture is reported to be miscible. In those cases where two liquid phases were observed, but with one of the liquid phases occupying only a very small volume, the mixture is reported to be partially miscible.

The polyalkylene glycol and ester oil lubricants were judged to be miscible in all tested proportions over the entire temperature range, except that for the HFO-1225ye mixtures with polyalkylene glycol, the refrigerant mixture was found to be immiscible over the temperature range of −50° C. to −30° C. and to be partially miscible over from −20 to 50° C. At 50 weight percent concentration of the PAG in refrigerant and at 60°, the refrigerant/PAG mixture was miscible. At 70° C., it was miscible from 5 weight percent lubricant in refrigerant to 50 weight percent lubricant in refrigerant.

Example 3

The compatibility of the refrigerant compounds and compositions of the present invention with PAG lubricating oils while in contact with metals used in refrigeration and air conditioning systems is tested at 350° C., representing conditions much more severe than are found in many refrigeration and air conditioning applications.

Aluminum, copper and steel coupons are added to heavy walled glass tubes. Two grams of oil are added to the tubes. The tubes are then evacuated and one gram of refrigerant is added. The tubes are put into an oven at 350° F. for one week and visual observations are made. At the end of the exposure period, the tubes are removed.

This procedure was done for the following combinations of oil and the compound of the present invention:
  a) HFO-1234ze and GM Goodwrench PAG oil
  b) HFO1243 zf and GM Goodwrench oil PAG oil
  c) HFO-1234ze and MOPAR-56 PAG oil
  d) HFO-1243 zf and MOPAR-56 PAG oil
  e) HFO-1225 ye and MOPAR-56 PAG oil.

In all cases, there is minimal change in the appearance of the contents of the tube. This indicates that the refrigerant compounds and compositions of the present invention are stable in contact with aluminum, steel and copper found in refrigeration and air conditioning systems, and the types of lubricating oils that are likely to be included in such compositions or used with such compositions in these types of systems.

Comparative Example

Aluminum, copper and steel coupons are added to a heavy walled glass tube with mineral oil and CFC-12 and heated for one week at 350° C., as in Example 3. At the end of the exposure period, the tube is removed and visual observations are made. The liquid contents are observed to turn black, indicating there is severe decomposition of the contents of the tube.

CFC-12 and mineral oil have heretofore been the combination of choice in many refrigerant systems and methods. Thus, the refrigerant compounds and compositions of the present invention possess significantly better stability with many commonly used lubricating oils than the widely used prior art refrigerant-lubricating oil combination.

Example 4

Polyol Foam

This example illustrates the use of blowing agent in accordance with one of the preferred embodiments of the present invention, namely the use of HFO-1234ze, and the production of polyol foams in accordance with the present invention. The components of a polyol foam formulation are prepared in accordance with the following table:

| | PBW |
|---|---|
| Polyol Component * | |
| Voranol 490 | 50 |
| Voranol 391 | 50 |
| Water | 0.5 |
| B-8462 (surfactant) | 2.0 |
| Polycat 8 | 0.3 |
| Polycat 41 | 3.0 |
| HFO-1234ze | 35 |
| Total | 140.8 |
| Isocyanate | |
| M-20S | 123.8 Index 1.10 |

* Voranol 490 is a sucrose-based polyol and Voranol 391 is a toluene diamine based polyol, and each are from Dow Chemical. B-8462 is a surfactant available from Degussa-Goldschmidt. Polycat catalysts are tertiary amine based and are available from Air Products. Isocyanate M-20S is a product of Bayer LLC.

The foam is prepared by first mixing the ingredients thereof, but without the addition of blowing agent. Two Fisher-Porter tubes are each filled with about 52.6 grams of the polyol mixture (without blowing agent) and sealed and placed in a refrigerator to cool and form a slight vacuum. Using gas burets, about 17.4 grams of HFO-1234ze are added to each tube, and the tubes are then placed in an ultrasound bath in warm water and allowed to sit for 30 minutes. The solution produced is hazy, a vapor pressure measurement at room temperature indicates a vapor pressure of about 70 psig, indicating that the blowing agent is not in solution. The tubes are then placed in a freezer at 27° F. for 2 hours. The vapor pressure was again measured and found to be 14-psig. The isocyanate mixture, about 87.9 grams, is placed into a metal container and placed in a refrigerator and allowed to cool to about 50° F. The polyol tubes were then opened and weighed into a metal mixing container (about 100 grams of polyol blend are used). The isocyanate from the cooled metal container is then immediately poured into the polyol and mixed with an air mixer with double propellers at 3000 RPM's for 10 seconds. The blend immediately begins to froth with the agitation and is then poured into an 8×8×4 inch box and allowed to foam. Because of the froth, a cream time cannot be measured. The foam has a 4-minute gel time and a 5-minute tack free time. The foam is then allowed to cure for two days at room temperature.

The foam is then cut to samples suitable for measuring physical properties and is found to have a density of 2.14 pcf. K-factors are measured and found to be as follows:

| Temperature | K, BTU In/Ft$^2$ h ° F. |
|---|---|
| 40° F. | .1464 |
| 75° F. | .1640 |
| 110° | .1808 |

Example 5

Polystyrene Foam

This example illustrates the use of blowing agent in accordance with two preferred embodiments of the present invention, namely the use of HFO-1234ze and HFO-1234-yf, and the production of polystyrene foam. A testing apparatus and protocol has been established as an aid to determining whether a specific blowing agent and polymer are capable of producing a foam and the quality of the foam. Ground polymer (Dow Polystyrene 685D) and blowing agent consisting essentially of HFO-1234ze are combined in a vessel. A sketch of the vessel is illustrated below. The vessel volume is 200 cm³ and it is made from two pipe flanges and a section of 2-inch diameter schedule 40 stainless steel pipe 4 inches long (see FIG. 1). The vessel is placed in an oven, with temperature set at from about 190° F. to about 285° F., preferably for polystyrene at 265° F., and remains there until temperature equilibrium is reached.

The pressure in the vessel is then released, quickly producing a foamed polymer. The blowing agent plasticizes the polymer as it dissolves into it. The resulting density of the two foams thus produced using this method are given in Table 1 and graphed in FIG. 1 as the density of the foams produced using trans-HFO-1234ze and HFO-1234yf. The data show that foam polystyrene is obtainable in accordance with the present invention. The die temperature for R1234ze with polystyrene is about 250° F.

TABLE 1

| T ° F. | Dow polystyrene 685D Foam density (lb/ft³) | |
|---|---|---|
|  | transHFO-1234ze | HFO-1234yf |
| 275 | 55.15 |  |
| 260 | 22.14 | 14.27 |
| 250 | 7.28 | 24.17 |
| 240 | 16.93 |  |

What is claimed is:

1. A method of transferring heat to or from a fluid or body to provide cooling of air in an automobile, said method comprising;
   (a) providing a heat transfer system comprising an automobile air conditioning system;
   (b) providing in said system a heat transfer composition comprising at least one lubricant and at least one -fluoroalkene of Formula II:

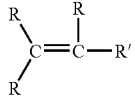

(II)

where
R' is (CR$_2$)$_n$Y,
Y is CF$_3$
each R is independently Cl, F, I or H
and n is 0 or 1,
provided that at least one of said Rs located on the unsaturated terminal carbon is H, wherein said fluoroalkene has no substantial acute toxicity.

2. The method of claim 1 wherein said unsaturated terminal carbon has one F substituent.

3. The method of claim 1 wherein n is 0.

4. The method of claim 3 wherein said unsaturated terminal carbon has no F substituent.

5. The method of claim 1 wherein each substituent on the unsaturated terminal carbon is H.

6. The method of claim 1 wherein n is 1.

7. The method of claim 1 wherein said fluoroalkene of Formula II comprises 1,1,1,2-tetrafluoropropene (HFO-1234yf).

8. The method of claim 1 wherein said fluoroalkene of Formula II comprises 1,3,3,3-tetrafluoropropene (HFO-1234ze).

9. The method of claim 1 wherein said fluoroalkene of Formula II comprises trans 1,3,3,3-tetrafluoropropene (HFO-1234ze).

10. The method of claim 1 comprising conditioning the air in an automobile comprising:
   (a) providing a vapor compression air conditioning system having at least one compressor, at least one condenser and a heat transfer composition in said system, said heat transfer composition comprising 1,1,1,2-tetrafluoropropene (HFO-1234yf) in an amount of from about 5% by weight to about 99% by weight of the heat transfer composition; and
   (b) operating said condenser in a temperature range that includes about 150° F.

11. The method of claim 1 wherein said at least one fluoroalkene consists essentially of 1,1,1,2-tetrafluoropropene (HFO-1234yf).

12. The method of claim 1 wherein said lubricant is present in the composition in an amount of from about 30 to about 50% by weight of the heat transfer composition based on the total weight of said lubricant and said compound(s) of Formula II.

13. The method of claim 1 wherein said lubricant is selected from the group consisting of polyol esters, polyalkylene glycols, polyalkylene silicon oils, mineral oils, alkyl benzenes, poly(alpha-olefins) and combinations of these.

14. The method of claim 1 wherein said lubricant comprises at least one polyalkylene glycol.

15. The method of claim 1 wherein said lubricant comprises polyalkylene glycol ester.

16. The method of claim 1 wherein said heat transfer composition has a Global Warming Potential (GWP) of not greater than about 150.

17. The method of claim 1 wherein said heat transfer composition has a Global Warming Potential (GWP) of not greater than about 75.

18. The method of claim 1 wherein said heat transfer composition has an ozone depletion potential (ODP) of not greater than about 0.05.

19. The method of claim 1 wherein said heat transfer composition has an ozone depletion potential (ODP) of not greater than about 0.02.

20. The method of claim 1 wherein said heat transfer composition has an ozone depletion potential (ODP) of not greater than about zero.

21. The method claim wherein said compound of Formula II is present in the composition in an amount of from about 5% by weight to about 95% by weight.

22. The method of claim 1 wherein said compound of Formula II is present in the composition in an amount of at least about 50% by weight.

23. The method of claim 1 wherein said compound of Formula II is present in the composition in an amount of at least about 70% by weight.

24. The method of claim 1 wherein said heat transfer composition further comprises one or more of the following: difluoromethane (HFC-32); pentafluoroethane (HFC-125); 1,1,2,2-tetrafluoroethane (HFC-134); 1,1,1,2-tetrafluoroethane (HFC-134a); difluoroethane (HFC-152a); 1,1,1,2,3,3,3-heptafluoropropane (HFC-227ea); 1,1,1,3,3,3-hexafluoropropane (HFC-236fa); 1,1,1,3,3-pentafluoropropane (HFC-245fa); 1,1,1,3,3-pentafluorobutane (HFC-365mfc); water; and CO$_2$.

25. The method of claim 1 wherein said heat transfer composition further comprises a flammability suppressant.

26. The method of claim 25 wherein said flammability suppressant comprises CF3I.

27. The method of claim 1 wherein said lubricant comprises an alkyl benzene.

28. The method of claim 1 wherein said lubricant comprises an ester oil.

29. The method of claim 1 wherein said lubricant comprises a poly(alpha-olefin) oil.

30. The method of claim 1 wherein said heat transfer composition has one liquid phase at at least one temperature between about −50° C. and +70° C.

31. The method of claim 1 wherein said heat transfer composition is stable when in contact with aluminum, steel and copper under the conditions of use in said air conditioning systems.

32. The method of claim 1 wherein heat transfer composition comprises from about 5% by weight to about 95% by weight of 1,1,1,2-tetrafluoropropene (HFO-1234yf).

33. A method of providing an air conditioning system for conditioning the air in an automobile comprising:
  (a) providing in the automobile a vapor compression air conditioning system having at least one compressor and at least one condenser; and
  (b) providing a refrigerant in said system for cooling the air in the automobile, said refrigerant comprising from about 5% by weight to about 99% by weight of 1,1,1,2-tetrafluoropropene (HFO-1234yf).

34. The method of claim 33 wherein said refrigerant further comprises at least one lubricant comprising a polyalkylene glycol.

35. The method of claim 34 wherein said refrigerant has one liquid phase at at least one temperature between about −50° C. and +70° C. and wherein said refrigerant has a a capacity relative to HFC-134a of about 1, a Coefficient of Performance (COP) relative to HFC-134a of about 1 and a Global Warming Potential (GWP) of not greater than about 75.

36. A method for cooling air in an automobile by use of an automobile air conditioning system, said method comprising providing in said automobile air conditioning system a heat transfer composition comprising at least one tetrafluoropropene according to Formula II:

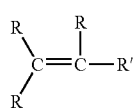

(II)

where
  R' is $(CR_2)_n Y$,
  Y is $CF_3$
  each R is independently F or H
  and n is 0,
  provided that at least one of said Rs located on the unsaturated terminal carbon is H.

37. The method of claim 36 wherein said tetrafluoropropene comprises 1,1,1,2-tetrafluoropropene (HFO-1234yf).

38. The method of claim 37 wherein said heat transfer composition comprises from about 5% by weight to about 95% by weight of 1,1,1,2-tetrafluoropropene (HFO-1234yf).

39. The method of claim 37 wherein said tetrafluoropropene consists essentially of 1,1,1,2-tetrafluoropropene (HFO-1234yf).

40. The method of claim 36 wherein said heat transfer composition further comprises at least one lubricant.

41. The method of claim 40 wherein said lubricant is selected from the group consisting of polyol esters, polyalkylene glycols, polyalkylene silicon oils, mineral oils, alkyl benzenes, poly(alpha-olefins) and combinations of these.

42. The method of claim 40 wherein said at least one lubricant comprises at least one polyalkylene glycol.

43. The method of claim 40 wherein said at least one lubricant comprises polyalkylene glycol ester.

44. The method of claim 41 wherein said heat transfer composition has one liquid phase at at least one temperature between about −50° C. and +70° C. and wherein said heat transfer composition has a capacity relative to HFC-134a of about 1 and a Coefficient of Performance (COP) relative to HFC-134a of about 1.

45. The method of claim 44 wherein said 1,1,1,2-tetrafluoropropene (HFO-1234yf) is present in the composition in an amount of at least about 70% by weight.

46. The method of claim 45 wherein said heat transfer composition further comprises one or more of the following: difluoromethane (HFC-32); pentafluoroethane (HFC-125); 1,1,2,2-tetrafluoroethane (HFC-134); 1,1,1,2-tetrafluoroethane (HFC-134a); difluoroethane (HFC-152a); 1,1,1,2,3,3,3-heptafluoropropane (HFC-227ea); 1,1,1,3,3,3-hexafluoropropane (HFC-236fa); 1,1,1,3,3-pentafluoropropane (HFC-245fa); 1,1,1,3,3-pentafluorobutane (HFC-365mfc); water; and $CO_2$.

47. A method for cooling the air in an automobile comprising:
  (a) providing in said automobile a vapor compression air conditioning system having at least one compressor and at least one condenser operable in a temperature range that includes about 150° F.; and
  (b) providing a heat transfer fluid in said system, said heat transfer fluid comprising 1,1,1,2-tetrafluoropropene (HFO-1234yf) in an amount of from about 5% by weight to about 99% by weight of the heat transfer fluid.

48. The method of claim 47 wherein said heat transfer fluid has a capacity relative to HFC-134a of about 1 and a Coefficient of Performance (COP) relative to HFC-134a of about 1.

49. The method of claim 47 wherein said heat transfer fluid further comprises at least one lubricant selected from the group consisting of polyol esters, polyalkylene glycols, polyalkylene silicon oils, mineral oils, alkyl benzenes, poy(alpha-olefins) and combinations of these.

50. A method of conditioning the air in an automobile using an automobile air conditioning system including at least one compressor and at least one evaporator, said method comprising:
  (a) utilizing in said system a heat transfer fluid comprising 1,1,1,2-tetrafluoropropene (HFO-1234yf) in an amount of from about 5% by weight to about 99% by weight of the heat transfer fluid; and
  (b) using said heat transfer fluid to absorb heat from the air in the automobile by evaporating in said evaporator said heat transfer fluid to produce a vapor comprising said HFO-1234yf;

(c) compressing at least a portion of said vapor from said step (b) in said at least one compressor to produce a relatively elevated pressure vapor comprising HFO-1234yf; and (d) removing heat from said relatively elevated pressure vapor by condensing said vapor.

51. The method of claim 50 wherein said heat transfer fluid further comprises at least one lubricant selected from the group consisting of polyol esters, polyalkylene glycols, polyalkylene silicon oils, mineral oils, alkyl benzenes, poy(alpha-olefins) and combinations of these and wherein said system further comprises a condenser operated in a temperature range that includes about 150° F.

52. The method of claim 51 wherein said heat transfer fluid has a Global Warming Potential (GWP) of not greater than about 75.

* * * * *